(12) United States Patent
Chow et al.

(10) Patent No.: US 12,000,820 B2
(45) Date of Patent: Jun. 4, 2024

(54) MULTIFUNCTIONAL AND MODULAR GEOTECHNICAL TESTING DEVICE

(71) Applicant: The Hong Kong University of Science and Technology, Hong Kong (CN)

(72) Inventors: Jun Kang Chow, Hong Kong (CN); Yu Hsing Wang, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 646 days.

(21) Appl. No.: 17/248,559

(22) Filed: Jan. 29, 2021

(65) Prior Publication Data

US 2021/0263007 A1     Aug. 26, 2021

Related U.S. Application Data

(60) Provisional application No. 63/100,057, filed on Feb. 26, 2020.

(51) Int. Cl.
| | |
|---|---|
| *G01N 33/24* | (2006.01) |
| *G01N 1/08* | (2006.01) |
| *G01N 1/10* | (2006.01) |

(52) U.S. Cl.
CPC ............. *G01N 33/246* (2013.01); *G01N 1/08* (2013.01); *G01N 2001/1062* (2013.01)

(58) Field of Classification Search
CPC ........ G01N 33/24; G01N 3/08; G01N 33/246; G01N 2203/0085; G01N 1/08; G01N 2001/1062

(Continued)

(56) References Cited

U.S. PATENT DOCUMENTS

| | | |
|---|---|---|
| 3,448,608 A | 6/1969 | Bishop et al. |
| 3,635,078 A | 1/1972 | Wissa |

(Continued)

FOREIGN PATENT DOCUMENTS

| | | | |
|---|---|---|---|
| CN | 108333060 A | * | 7/2018 |
| CN | 110186787 A | | 8/2019 |

(Continued)

OTHER PUBLICATIONS

Pan, Z., Ma, Y., Connell, L.D., Down, D.I. and Camilleri M. (2015). Measuring anisotropic permeability using a cubic shale sample in a triaxial cell. Journal of Natural Gas Science and Engineering, 26, 336-344.

(Continued)

*Primary Examiner* — Daniel S Larkin
*Assistant Examiner* — Nashmiya S Fayyaz
(74) *Attorney, Agent, or Firm* — S&F/WEHRW

(57) ABSTRACT

A multifunctional and modular geotechnical testing device for testing a soil sample is provided. The testing device includes a testing cell, a plurality of needle probes, and a plurality of lateral pressure-measuring sensors. The testing cell has an oedometer ring for accommodating the soil sample, with a plurality of holes located on and angularly distributed over an internal lateral surface of the oedometer ring forming a plurality of channels to access the soil sample from outside. The plurality of needle probes, each configured to house a pore water pressure-measuring sensor, is detachably mountable to the plurality of channels from outside for simultaneously measuring the pore water pressures. The plurality of lateral pressure-measuring sensors is removably attachable to an inner peripheral side of the testing cell for measuring lateral pressures of the soil sample.

21 Claims, 12 Drawing Sheets

(58) Field of Classification Search
USPC .............................................. 73/818, 38, 784
See application file for complete search history.

(56) References Cited

U.S. PATENT DOCUMENTS

| | | | |
|---|---|---|---|
| 9,567,722 B2 | 2/2017 | Gupta | |
| 2009/0049924 A1* | 2/2009 | Ng | G01N 33/24 |
| | | | 73/818 |
| 2010/0089124 A1* | 4/2010 | Katti | E02D 1/027 |
| | | | 73/38 |

FOREIGN PATENT DOCUMENTS

| | | | |
|---|---|---|---|
| CN | 110487988 A | | 11/2019 |
| EP | 1493995 A1 | | 1/2005 |
| RU | 86199 U1 | * | 8/2009 |
| RU | 92958 U1 | * | 4/2010 |
| RU | 2416081 C1 | * | 4/2011 |
| RU | 2423682 C1 | * | 7/2011 |
| SU | 939638 A1 | * | 6/1982 |
| SU | 1118900 A | * | 10/1984 |
| SU | 1425538 A1 | * | 9/1988 |
| WO | 2020048408 A1 | | 3/2020 |

OTHER PUBLICATIONS

Melissa E. Landon, Chistopher Marchetti and Don J. DeGroot. Constant Rate of Strain Consolidation Testing of Saturated Cohesive Soils Without Back Pressure Saturation. Geotechnical Testing Journal, vol. 41, No. 2, Mar. 2018, 425-433.
C. Colreavy, C. D. O'Loughlin and M. F. Randolph. Estimating consolidation parameters from field piezoball tests. (2016). Géotechnique 66, No. 4, 333-343.

* cited by examiner

MULTIFUNCTIONAL AND MODULAR GEOTECHNICAL TESTING DEVICE

CROSS-REFERENCE TO RELATED APPLICATIONS

This application claims the benefit of U.S. Provisional Patent Application No. 63/100,057, filed on Feb. 26, 2020, which is incorporated by reference herein in its entirety.

LIST OF ABBREVIATIONS AND SYMBOLS $\Delta u$ Excess pore water pressure
$\Delta u_{peak}$ Maximum measured $\Delta u$
$\Delta u_{peak}/\Delta u_0$ Maximum measured $\Delta u$ to the increment of applied loading
(S-t) Settlement-time data
(U-$T_v$) Average degree of consolidation-theoretical time factor
BS 1377 British Standard 1377
$c_v$ Coefficient of consolidation
LVDT Linear variable displacement transducer
k Coefficient of permeability
$K_0$ Coefficient of Earth pressure at rest

FIELD OF THE INVENTION

The present disclosure generally relates to a testing device for geotechnical engineering, and particularly relates to a multifunctional and modular geotechnical testing device for performing an all-purpose soil characterization.

BACKGROUND OF THE INVENTION

Geotechnical engineering plays an important role in designing building foundations. This is heralded as an art today because of the economic impracticalities to characterize the entire underlying intricacies of soil strata. The ever-incomplete picture thus necessitates the input of a large amount of human experience for: (1) selecting borehole locations for site characterizations or subsurface investigation; (2) designing appropriate foundations from the inference of substrata borehole information; and (3) reactively revising the design during the construction as previously unforeseen and unpredictable local soil properties are discovered. Inadequate human experience at each and every stage of the engineering practice, as often so happen, boils down to one single crucial problem, which is a lack of soil characterization data at scale.

Terzaghi's theory of one-dimensional consolidation is well developed and has been widely used for decades to describe the soil consolidation process [19], [36]. Although this theory is used to describe the dissipation of $\Delta u$ due to applied loading, $\Delta u$ is not generally measured, and only the settlement is measured in conventional oedometer tests. Furthermore, the associated consolidation parameters, such as the $c_v$, are commonly determined based on the settlement measurements. In this regard, the curve fitting technique, i.e., comparing the distinct features between the (S-t) and the (U-$T_v$), has been widely used. Among these methods, the log-time method [7] and the root-time method [34] are most commonly used in practice. Despite the simplicity of analysis, based on the settlement data, the reliability of $c_v$ obtained from these two methods is often questioned. In addition, according to the studies carried out by Sebai and Belkacemi [28], a wide discrepancy in the values of $c_v$ were obtained by 38 professional engineers, even though the same method was used.

The presence of discrepancies in estimating $c_v$ is mainly due to biased judgement in identifying the points of interest [4], [15], [30], [33] and the influences of the immediate and secondary compressions [2], [3], [9], [16], [20], [21], [24], [32], [37]. To resolve this issue, different approaches, such as the rectangular hyperbola method [33], velocity method [16] and inflection point method [17], were developed to enhance the reliability of the estimated $c_v$. However, significant deviations still occur in the $c_v$ determined using different approaches [2], [15].

Furthermore, attempts were previously made to directly or indirectly determine the $c_v$ based on the measured $\Delta u$ during the one-dimensional consolidation tests [6], [12]. However, several challenges were encountered. First, to enable pore water pressure measurement, the testing device has to be modified, in which the base is changed to an impervious boundary to ease the $\Delta u$ measurement [25], [26], [39]. Unfortunately, the required modifications involve complicated and precise manufacturing processes, which hinder consolidation tests when applying the modified devices in routine usage. In addition, measurement bias is found in the $\Delta u$ measurements gauged by such modified devices. Compared to the theoretical response, the actual measurement exhibits a time-lag, i.e., a time delay in measuring the maximum pore water pressure, with a smaller peak value; such a response has been reported in a number of published results [1], [14], [22], [41]. This observation is mostly related to the low volumetric compliance of the pore water pressure measuring system, which is also known as system flexibility [11], [13], [41]. In response to the applied loading, i.e., the generation of the excess pore water pressure, the connecting tube expands and the diaphragm of the pressure transducer deflects, creating a temporary drainage boundary. Before pressure equilibrium is reached, a flow of water occurs, and certainly this flow takes time, which in turn induces bias in the $\Delta u$ measurement. The amount of the time-lag and the ratio of the $\Delta u_{peak}/\Delta u_0$ are found to vary for different types of soil samples subjected to different levels of vertical stresses [12], [25], [39]. To a certain extent, this measurement bias also hinders the wide usage of the measured $\Delta u$ to determine $c_v$. Further, even though the evolution of $\Delta u$ can be measured and recorded, the determination of $c_v$ still relies on a single time point only, which is likely to be insufficiently representative to reflect the whole consolidation process. For instance, as suggested in BS 1377 [5], in adopting the Rowe cell (also called the hydraulic cell) to determine $c_v$, only a single time point corresponding to the average degree of consolidation of 50% (i.e., $t_{50}$) is used [27]. Hence, there is an urgent need for developing feasible methods to determine $c_v$, without a need for decision subjectivity of the users.

Furthermore, additional measurement of other properties during consolidation, such as the k and the $K_0$ of the soil samples, allows relatively quick and easy analyses of the soil properties during consolidation. However, the existing methods of conducting separate constant head or falling head tests to determine k and modifying existing equipment to obtain $K_0$ are generally complicated in preparation and calibration [18], [29], [35], [38], [40], [42].

Accordingly, there is a need in the art for a testing device that seeks to address at least some of the above long-lasting problems and limitations encountered in conventional oedometer testing. Furthermore, other desirable features and characteristics will become apparent from the subsequent detailed description and the appended claims, taken in conjunction with the accompanying drawings and this background of the disclosure.

SUMMARY OF THE INVENTION

Provided herein are a multifunctional and modular geotechnical testing device for performing an all-purpose soil characterization. It is an objective of the present disclosure to provide a testing device for testing a soil sample, which can be used to determine various kind of soil properties of the soil sample.

In accordance with certain embodiments of the present disclosure, the testing device includes a testing cell and a plurality of needle probes. The testing cell includes an oedometer ring for accommodating the soil sample. The oedometer ring including a plurality of holes located on and angularly distributed over an internal lateral surface of the oedometer ring. The plurality of holes forming a plurality of channels to access the soil sample from outside the oedometer ring for measuring pore water pressures at plural selected angles of the oedometer ring. The plurality of needle probes is detachably mountable to the plurality of channels from outside the oedometer ring. The plurality of needle probes are configured to simultaneously measure the pore water pressures at the selected angles of the oedometer ring for avoiding adverse effects due to time-lag when compared to sequential measurements of the pore water pressures. The plurality of needle probes is configured to house a plurality of pore water pressure-measuring sensors used for performing simultaneous measurement of the pore water pressures.

In accordance with a further aspect of the present disclosure, the testing device includes a plurality of lateral pressure-measuring sensors removably attachable to an inner peripheral side of the testing cell. The plurality of lateral pressure-measuring sensors is arranged to be located at plural selected locations of the inner peripheral side of the testing cell for measuring lateral pressures of the soil sample at the selected locations when the plurality of lateral pressure-measuring sensors is immersed in the soil sample.

In accordance with a further aspect of the present disclosure, an individual needle probe is accessible to the soil sample through a respective hole for measuring a corresponding pore water pressure present at the respective hole. Each individual needle probe comprises a barrel for filling with de-aired water, a tube insertable into the respective hole, a plunger coupled to the barrel, and a sensor holder. The tube is coupled to the barrel for receiving the de-aired water such that the de-aired water is accessible to the soil sample. The plunger pushes the de-aired water forward to fill up the individual needle probe so as to remove air bubbles from the individual needle probe, causing the de-aired water to be pressurized from the pore water. The sensor holder is configured to receive a respective pore water pressure-measuring sensor and position the respective pore water pressure-measuring sensor into the barrel, allowing the respective pore water pressure-measuring sensor to measure the corresponding pore water pressure.

Preferably, the testing device comprises the plurality of pore water pressure-measuring sensors for measuring the pore water pressures at the selected angles of the oedometer ring.

Preferably, the plurality of pore water pressure-measuring sensors and the plurality of lateral pressure-measuring sensors use pressure-measuring sensors of a same type.

Preferably, the individual needle probe further comprises a stiff O-ring positioned at an end of the plunger and used as a plunger stopper for sealing the individual needle probe, thereby preventing the de-aired water from flowing out or air from flowing into the individual needle probe.

In accordance with a further aspect of the present disclosure, the plurality of holes is substantially-evenly distributed angularly over the internal lateral surface of the oedometer ring.

Preferably, the plurality of holes consists of three holes.

In accordance with a further aspect of the present disclosure, an individual hole comprises a channel and a large-diameter end for placing of filter materials to avoid clogging.

In accordance with a further aspect of the present disclosure, the testing cell further comprises a top flange for holding the oedometer ring in position and preventing any external interference that potentially changes boundaries and loading conditions of the soil sample.

In accordance with a further aspect of the present disclosure, the testing cell further comprises a cutting tool mountable on the oedometer ring for trimming the soil sample to be used in testing.

Preferably, the cutting tool is made of stainless steel.

Preferably, the oedometer ring further includes a plurality of grooves configured to receive the cutting tool for securing the cutting tool to the oedometer ring.

In accordance with a further aspect of the present disclosure, the respective hole has a diameter greater than a diameter of the tube of the individual needle probe by at least 1 mm for avoiding clogging of soil particles. The respective hole has a length at least 0.5 mm longer than a length of the tube for allowing filtering materials to be placed in the respective hole.

In accordance with a further aspect of the present disclosure, an individual lateral pressure-measuring sensor is a piezoresistive force sensor or a piezoelectric force sensor.

In accordance with a further aspect of the present disclosure, an individual lateral pressure-measuring sensor is coated with three polyurethane coatings and a super hydrophobic coating for waterproofing the individual lateral pressure-measuring sensor.

In accordance with a further aspect of the present disclosure, the respective pore water pressure-measuring sensor is a piezoresistive force sensor or a piezoelectric force sensor.

In accordance with a further aspect of the present disclosure, the respective pore water pressure-measuring sensor is coated with three or four polyurethane coatings and a super hydrophobic coating for waterproofing the respective pore water pressure-measuring sensor.

In accordance with a further aspect of the present disclosure, the oedometer ring is cylindrical in shape such that the soil sample is in a form of disc.

In accordance with a further aspect of the present disclosure, a stress-applying mechanism for applying a stress to the soil sample to compress the soil sample. A displacement-measuring sensor for sensing a displacement made in compressing the soil sample.

Preferably, the displacement-measuring sensor is a dial gauge or a linear variable displacement transducer.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Other aspects and advantages of the present invention are disclosed as illustrated by the embodiments hereinafter.

BRIEF DESCRIPTION OF THE DRAWINGS

The appended drawings contain figures to further illustrate and clarify the above and other aspects, advantages, and features of the present disclosure. It will be appreciated that these drawings depict only certain embodiments of the present disclosure and are not intended to limit its scope. It will also be appreciated that these drawings are illustrated for simplicity and clarity and have not necessarily been depicted to scale. The present disclosure will now be described and explained with additional specificity and detail through the use of the accompanying drawings in which.

DETAILED DESCRIPTION OF THE INVENTION

The following detailed description is merely exemplary in nature and is not intended to limit the disclosure or its application and/or uses. It should be appreciated that a vast number of variations exist. The detailed description will enable those of ordinary skilled in the art to implement an exemplary embodiment of the present disclosure without undue experimentation, and it is understood that various changes or modifications may be made in the function and structure described in the exemplary embodiment without departing from the scope of the present disclosure as set forth in the appended claims.

The benefits, advantages, solutions to problems, and any element(s) that may cause any benefit, advantage, or solution to occur or become more pronounced are not to be construed as a critical, required, or essential features or elements of any or all of the claims. The invention is defined solely by the appended claims including any amendments made during the pendency of this application and all equivalents of those claims as issued.

Figure 2:
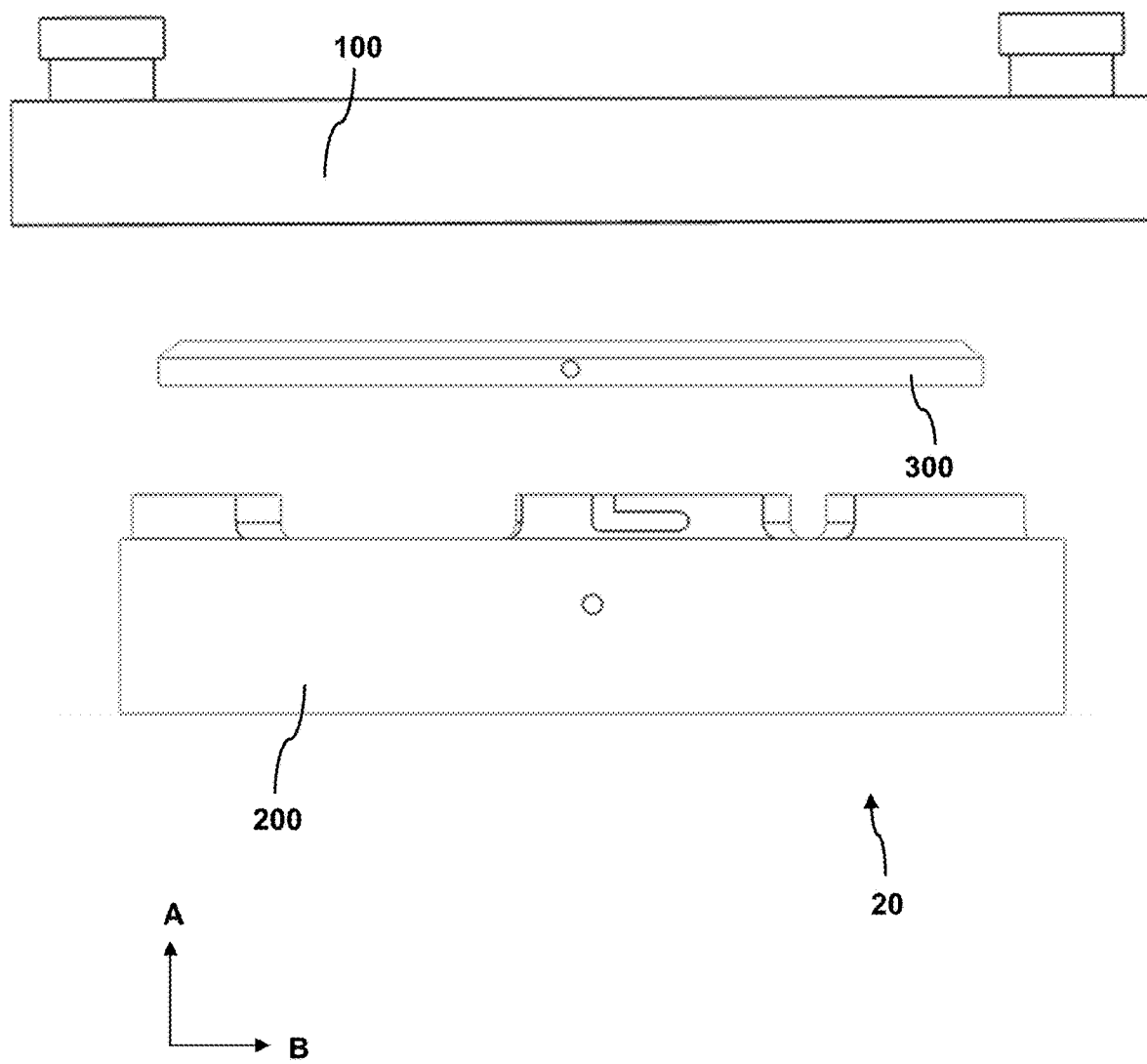
FIG. 2 depicts a side view of the testing cell in accordance with certain embodiments of the present disclosure.

Terms such as "upper", "lower", "inner", "outer", "top", "bottom", and variations thereof are used herein for ease of description to explain the positioning of an element, or the positioning of one element relative to another element, and are not intended to be limiting to a specific orientation or position. A vertical axis A is defined by the gravity as shown in FIG. 2, extending from the top of the testing cell 20 to the bottom of the testing cell 20. Furthermore, a longitudinal axis B that is substantially perpendicular to the vertical axis A is also defined.

The present disclosure generally relates to a multifunctional and modular geotechnical testing device for performing an all-purpose soil characterization. More specifically, but without limitation, the present disclosure relates to a testing device for testing a soil sample, which can be used to determine various kinds of soil properties of the soil sample.

The term "multifunctional" refers to a simultaneous measurement of various soil properties of geotechnical processes, for example, when conducting consolidation, shearing, wetting-and-drying, cementation, etc. It is the objective of the present disclosure to provide a more reliable, representative, and comparable information on the soil properties.

The term "modular" refers to various kinds of sensing modules that can be customized and utilized interchangeably for characterizing the soil properties. This is particularly essential for providing a testing platform suitable for executing various measurements of the soil sample in one test. In other words, the entire testing device is designed as a plug-and-play tool. Various kinds of sensing modules, such as pressure-based sensors, electromagnetic wave-based sensing system, and image-based measurement devices, can be easily installed and replaced according to the experimental need and requirement.

Figure 1:
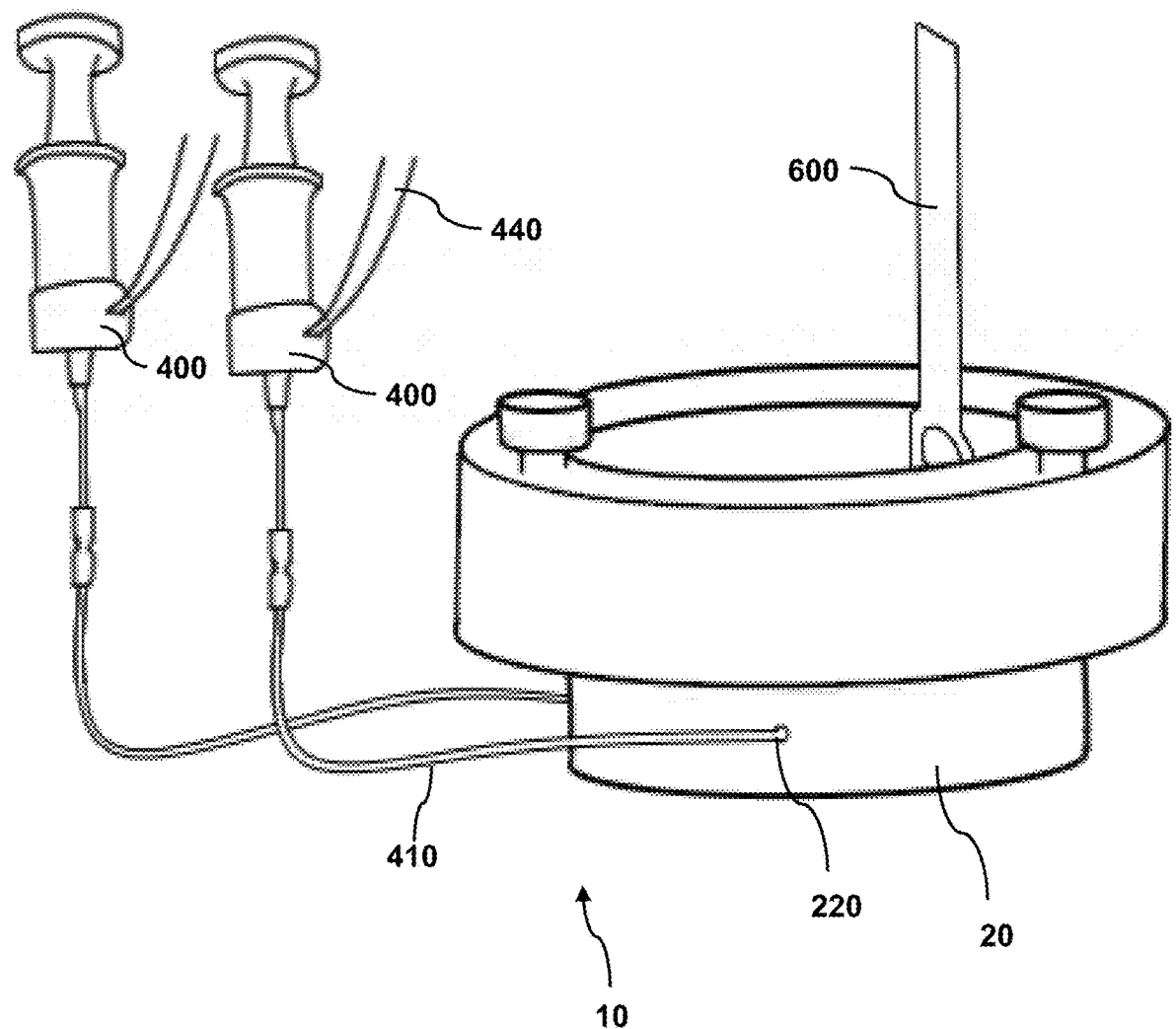
FIG. 1 is a conceptual diagram illustrating the multifunctional and modular geotechnical testing device in accordance with certain embodiments of the present disclosure.

As conceptually illustrated in FIG. 1, the present disclosure provides a novel geotechnical testing device, which is generally designated as 10, for testing a soil sample during consolidation. In certain embodiments, the testing device 10 is named as U-oedometer and configured to determine soil properties by performing simultaneous determination of $c_v$, k and $K_0$ during consolidation. In addition to the conventional settlement measurement, the testing device 10 augments the capabilities of conventional oedometer devices, i.e., renders pore water pressure and lateral pressure measurement for solving long-lasting problems in the determination of soil properties during consolidation. The testing device 10 comprises three parts, namely a testing cell 20, a pore water measuring system, and a lateral pressure measuring system. The testing cell 20 is arranged to accommodate the soil sample, which is the subject matter for testing. The pore water measuring system includes a plurality of needle probes 400 detachably mountable to the testing cell 20, each configured to house a pore water pressure-measuring sensor 440 for simultaneously measuring the pore water pressures. The lateral pressure measuring system includes a plurality of lateral pressure-measuring sensors 600 removably attachable to an inner peripheral side of the testing cell 20. Additionally, the testing device 10 may also include other conventional settlement measurement systems, such as a dial gauge and an LVDT.

The plurality of lateral pressure-measuring sensors 600 is arranged to be located at plural selected locations of the inner peripheral side of the testing cell 20 for measuring the lateral pressures of the soil sample at that selected locations when the plurality of lateral pressure-measuring sensors 600 is immersed in the soil sample. In certain embodiments, the lateral pressure-measuring sensor 600 is a piezoresistive force sensor or a piezoelectric force sensor. In one embodiment, the lateral pressure-measuring sensor 600 is a Flexiforce® sensor, which is a thin and flexible film-like piezoresistive force sensor. Flexiforce® sensor has a sensing range from 0 to 111N (equivalent to 0 to 1556 kPa), a sensing area of 9.53 mm in diameter, and a thickness of 0.203 mm. When a force is applied on the sensor, the output resistance changes, resulting in the varied output voltage measured corresponding to an applied force. It is apparent that the relative size between the soil particles and the sensing area could affect the measurement accuracy due to limited particles in contact with the sensor. The sensor can also be integrated into a force-to-voltage circuit, such that the sensor calibration can be established based on the applied force and output voltage.

In certain embodiments, waterproofing pre-treatment is applied to each of the plurality of lateral pressure-measuring sensors 600. As the plurality of lateral pressure-measuring sensors 600 is in direct contact to the soil sample, it is required to have at least a water repelling coating or layer thereon. The present disclosure provides a special coating for each individual lateral pressure-measuring sensor 600, comprising at least three polyurethane coatings and one outer layer of super hydrophobic coating. Preferably, each individual lateral pressure-measuring sensor 600 comprises three or four polyurethane coatings for making the lateral pressure-measuring sensor 600 waterproof. After the pre-treatment, each of the plurality of lateral pressure-measuring sensors 600 is calibrated for short-term static loading [10], which is required to first immerse into de-aired water in a sealed cubic box, followed by calibration by applying different pressure levels.

With reference to FIG. 2, the testing cell 20 comprises a top flange 100, an oedometer ring 200, and a cutting tool 300. In certain embodiments, the testing cell 20 is constructed by modifying the existing oedometer cell or settlement column, such that the testing cell 20 can be easily installed in and compatible with the conventional oedometer or other consolidation apparatuses for maximizing the potential usage. The oedometer is generally used for measuring the compression of a soil sample when the soil sample is subjected to a constant load or a stress. In one embodiment, the stress is applied to the soil sample from the top of the testing cell 20 along the vertical axis A to compress the soil sample.

Figure 3A:
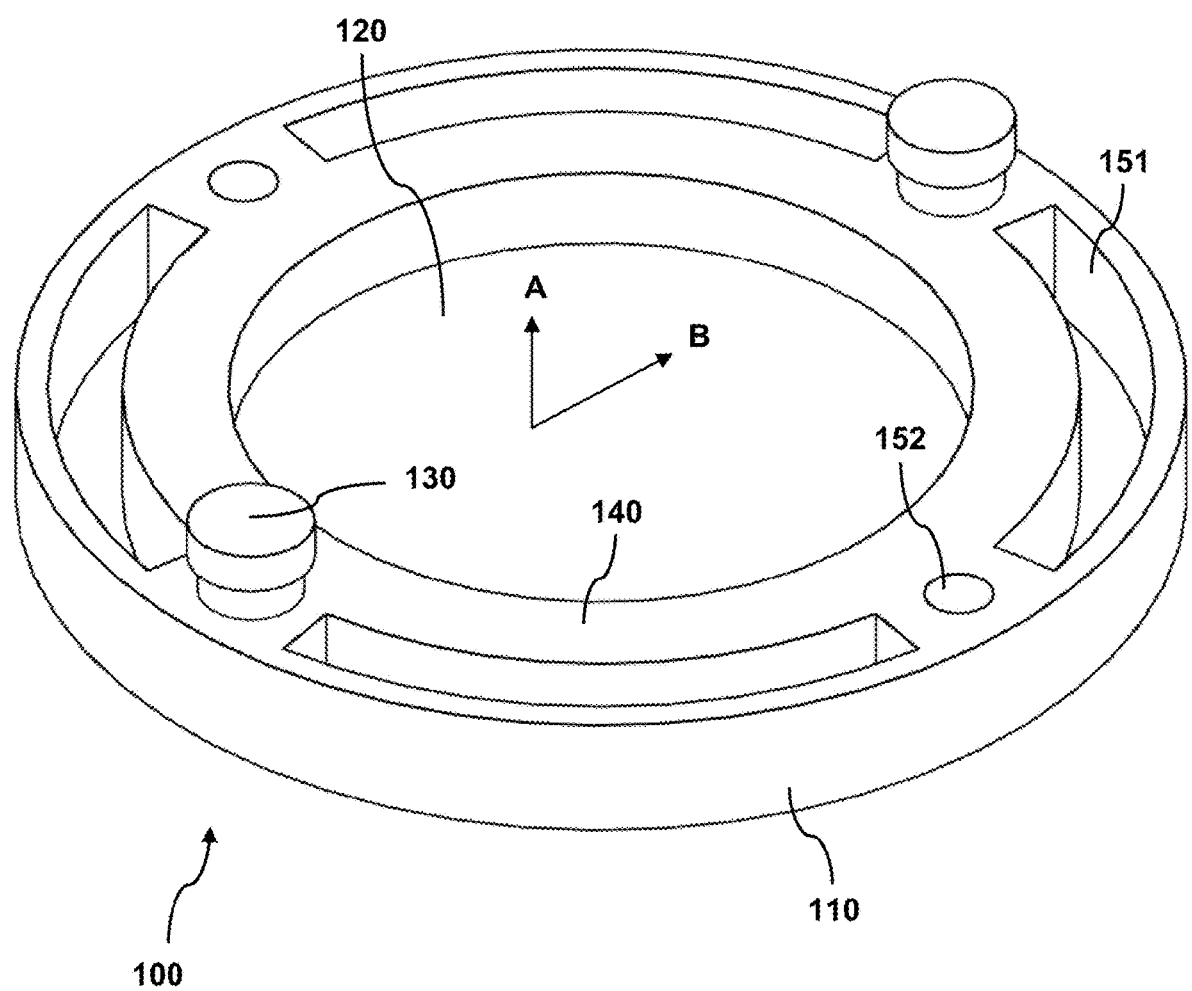
FIG. 3A depicts a perspective view of the top flange of the testing cell of FIG. 2.
Figure 3B:
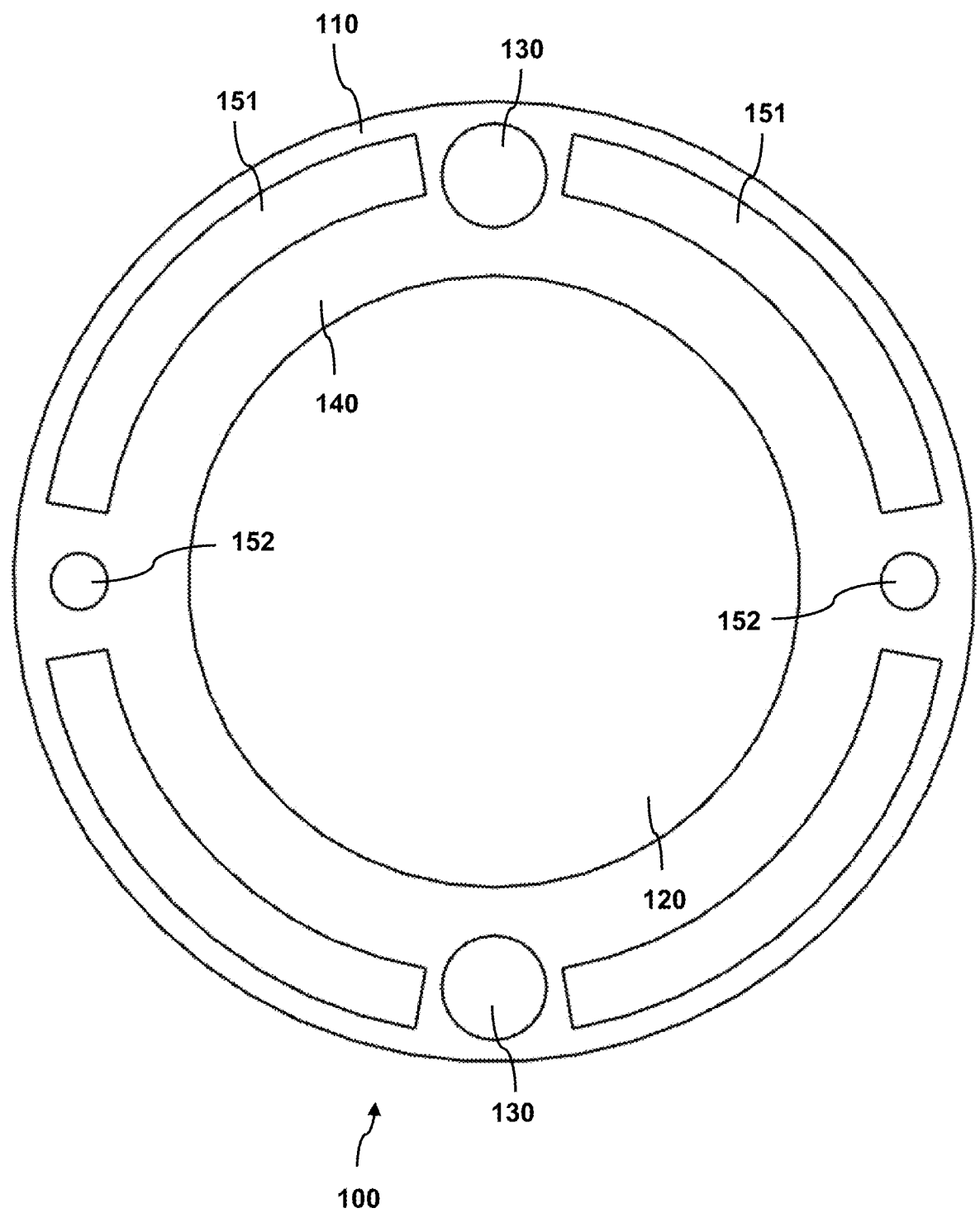
FIG. 3B depicts a top view of the top flange of FIG. 3A.

As illustrated in FIGS. 3A-3B and discussed in greater detail below, the top flange 100 or rim structure is provided for holding the oedometer ring 200 in position and preventing any external interference that potentially changes the boundaries and loading conditions of the soil sample. The top flange 100 may include a center opening 120, one or more peripheral long holes 151, one or more handle knobs 130, and one or more mounting holes 152 arranged circumferentially around the center opening 120. As divided by the peripheral long holes 151 and the mounting holes 152, the flange 100 can be provided with an outer ring 110 and an inner ring 140. In certain embodiments, the one or more handle knobs 130 are arranged along the longitudinal axis B.

Figure 4A:
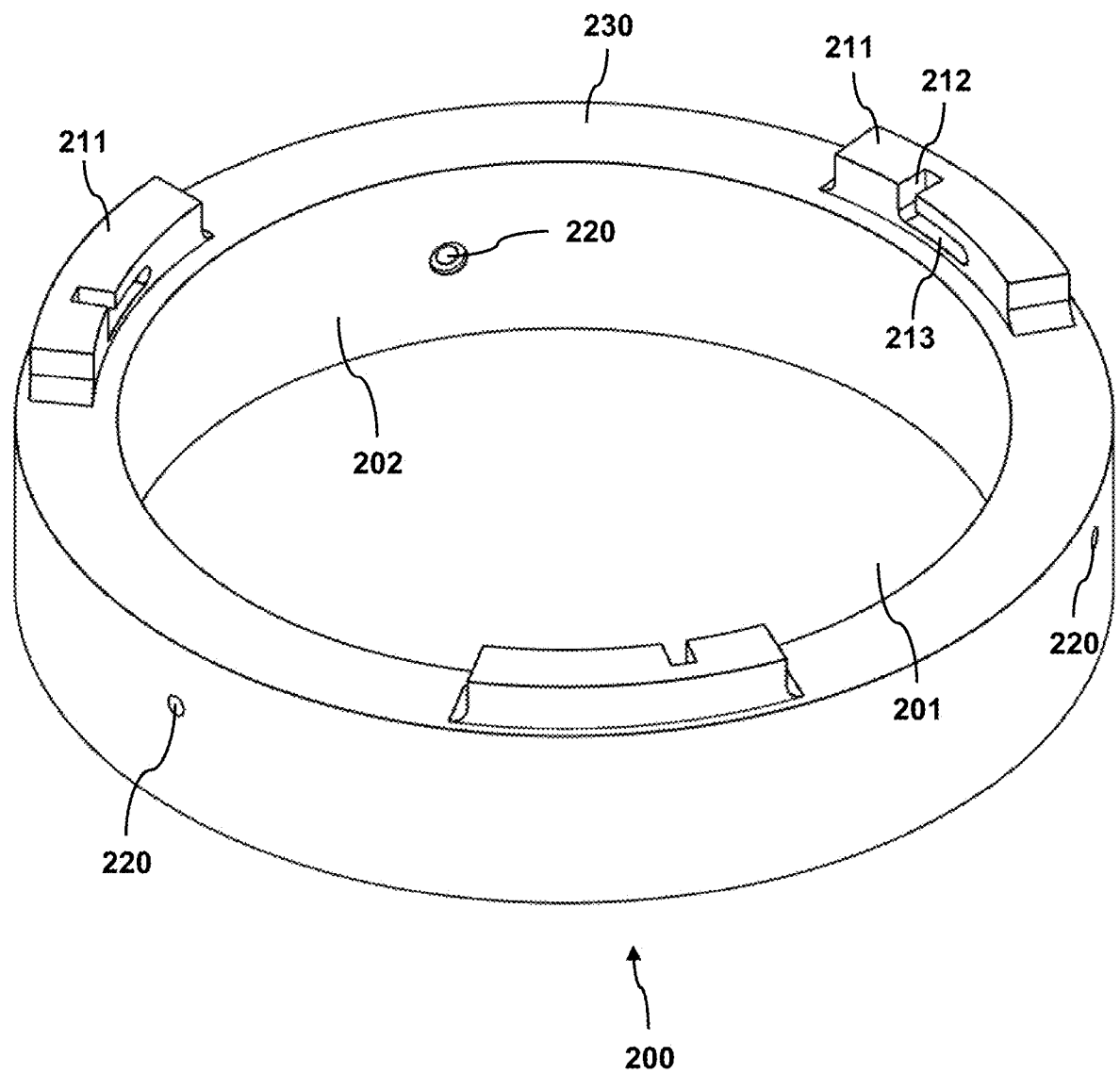
FIG. 4A depicts a perspective view of the oedometer ring of the testing cell of FIG. 2.

Referring to FIG. 4A, the oedometer ring 200 is a hollow column with an interior hollow space 201 for accommodating the soil sample. Therefore, the oedometer ring 200 is cylindrical in shape such that the soil sample is in a form of disc. Preferably, the diameter of the interior hollow space 201 is the same as the diameter of the center opening 120. The diameter of the interior hollow space 201 is approximately 70 mm and the oedometer ring 200 has a height of approximately 20 mm. It is apparent that the height of the oedometer ring 200 can be otherwise according to different testing requirements, and the shape may not be cylindrical in shape, for example, it can also be a rectangular column, an elliptical cylinder, a polygonal column, or any other shapes thereof. On the oedometer ring 200, there is a plurality of holes 220 located on and angularly distributed over an internal lateral surface 202 of the oedometer ring 200. In one embodiment, there are three holes 220 on the oedometer ring 200, while the three holes 220 are substantially-evenly distributed at 120 degrees apart over the internal lateral surface 202 of the oedometer ring 200. The plurality of holes 220 is preferably vertically positioned at or around the center of the internal lateral surface 202, thereby the holes 220 are used to determine the soil properties at the same depth to ensure an accurate measurement on a particular layer. In addition, the multiple measurements enhance fault-tolerance, where measurement of $\Delta u$ can still be obtained even if any of the pore water pressure-measuring sensor 440 malfunction.

Figure 4B:
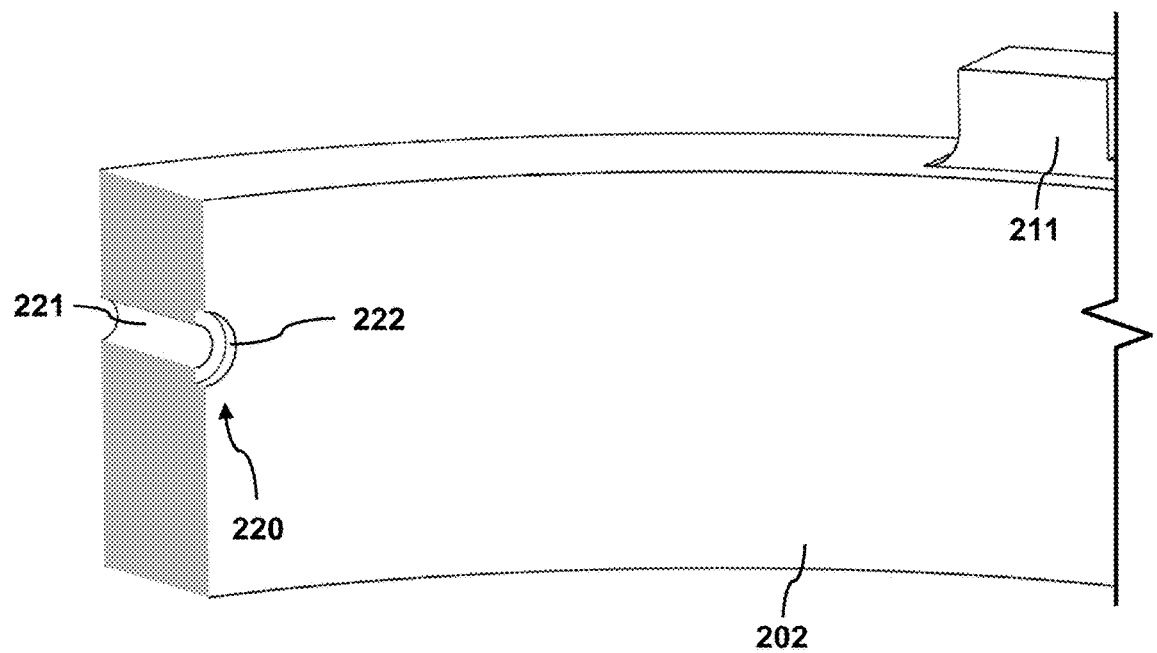
FIG. 4B depicts a cross-sectional view of hole located on and angularly distributed over the internal lateral surface of the oedometer ring of FIG. 4A.

From the cross-sectional view of a particular hole in FIG. 4B, the plurality of holes 220 forms a plurality of channels 221 to access the soil sample from outside the oedometer ring 200 such that pore water pressures at plural selected angles of the oedometer ring 200 are measurable when the soil sample is mixed with pore water. The $\Delta u$ during consolidation can be computed from the pole water pressure. To avoid clogging of the soil particles, the channel 221 of that particular hole is enlarged at the internal lateral surface 202 to form a large-diameter end 222 to allow placing of filter materials, such as filter papers and wire gauzes. In certain embodiments, the large-diameter end 222 is 3 mm in diameter and 0.5 mm in depth from the internal lateral surface 202 of the oedometer ring 200.

Figure 4C:
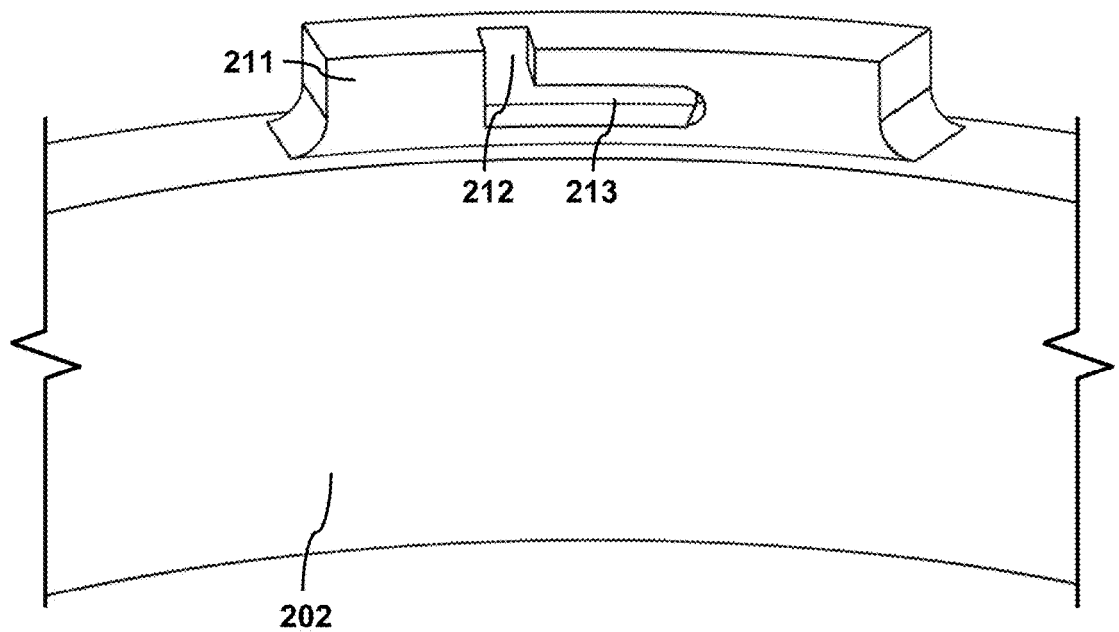
FIG. 4C depicts a side perspective view of the groove in the oedometer ring of FIG. 4A.
Figure 4D:
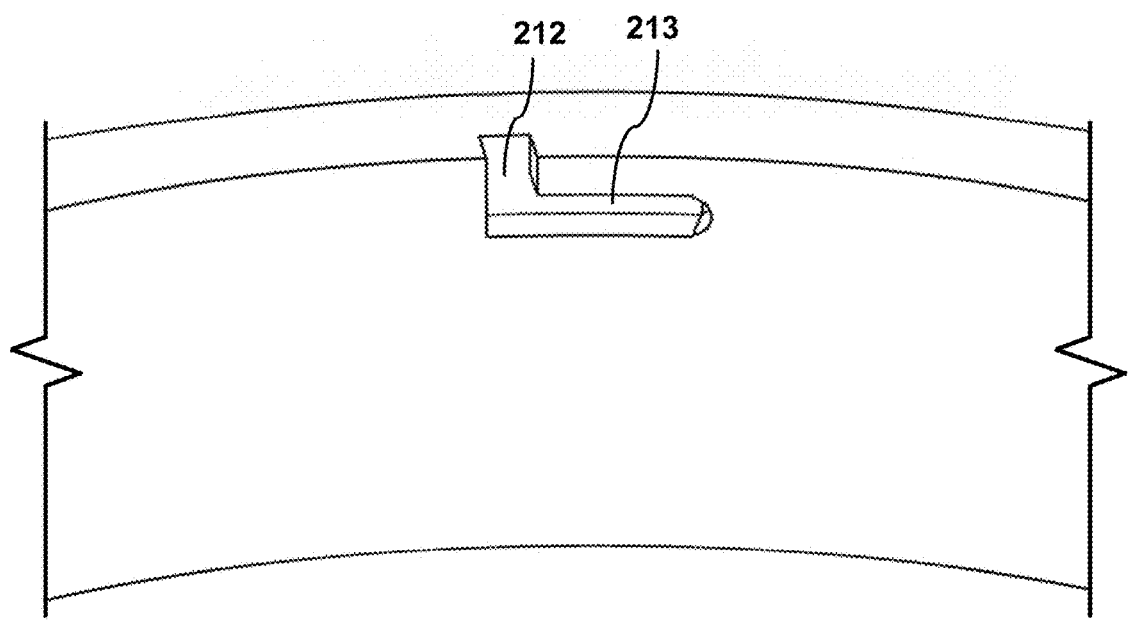
FIG. 4D depicts a side perspective view of the groove in the oedometer ring in accordance with certain alternative embodiments of the present disclosure.

For connecting to the cutting tool 300, the oedometer ring 200 further comprises a plurality of grooves 212 configured to receive the cutting tool 300 for securing the cutting tool 300 to the oedometer ring 200. FIG. 4C shows a preferred configuration of a particular groove 212. On the upper end of the oedometer ring 200, there is a plurality of protruding blocks 211. In one embodiment, the protruding block 211 is curved with a center of curvature equivalent to the cross-sectional center of the oedometer ring 200. On the inner side of each protruding block 211, there is provided the groove 212 with a slot 213 connected thereto, thereby the cutting tool 300 can be locked to the oedometer ring 200 firmly. The slot 213 may be arranged in different angles to the groove 212 other than the illustrated embodiment for firmly secure the cutting tool 300 without departing from the scope and spirit of the present disclosure. In FIG. 4D, an alternative embodiment of the groove 212 is illustrated. The groove may also be provided on the inner lateral surface 202 of the oedometer ring 200 without a protruding block 211. Therefore, the groove 212 and the slot 213 are substantially a cut-out from the oedometer ring 200.

Figure 5:
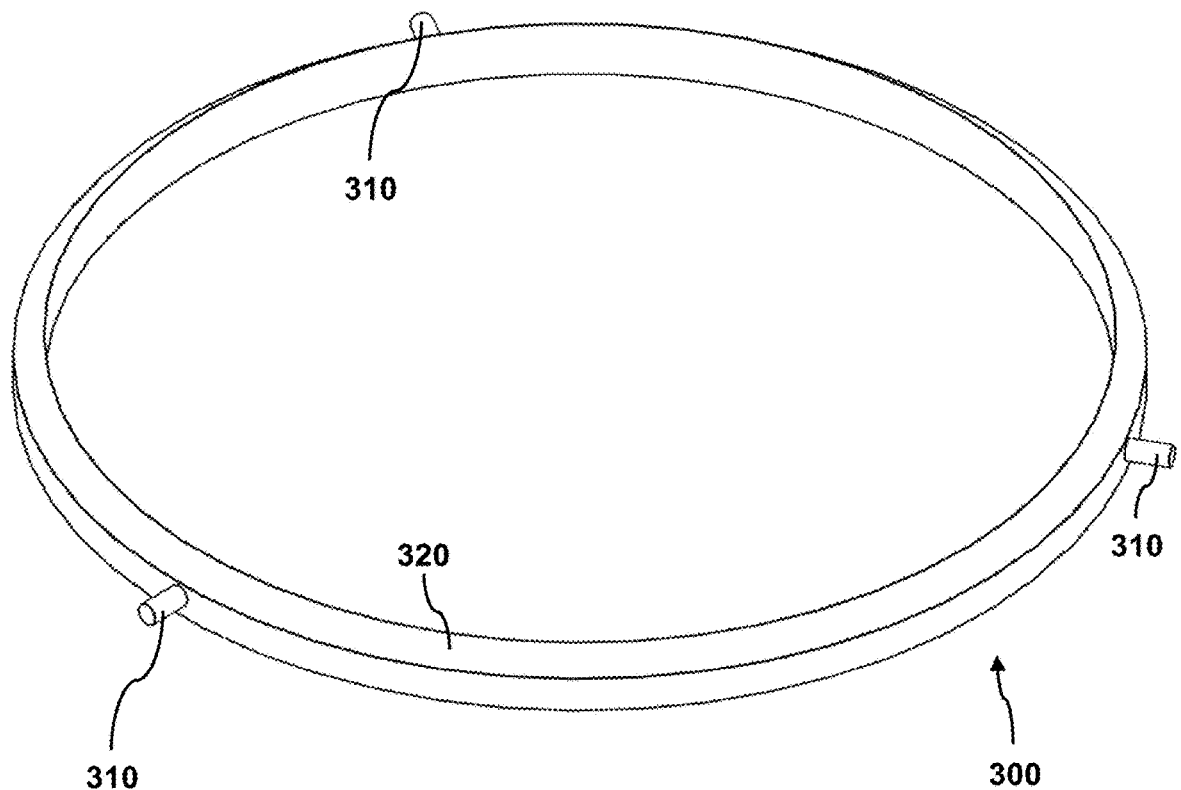
FIG. 5 depicts a perspective view of the cutting tool of the testing cell of FIG. 2.

The cutting tool 300 is preferably made of stainless steel, titanium, high strength alloy, or the like. The cutting tool 300 is mountable on the oedometer ring 200 for trimming the soil sample to be used in testing. FIG. 5 provides an exemplary illustration of the cutting tool 300 in accordance with certain embodiments of the present disclosure. The cutting tool 300 comprises a ring body 320 and a plurality of pins 310, wherein the plurality of pins 310 is circumferentially arranged, and substantially-evenly distributed angularly around the ring body 320. In certain embodiments, the plurality of pins 310 is distributed in the same manner angularly as the plurality of grooves 212 such that the plurality of grooves 212 can receive the plurality of pins 310 to secure the cutting tool 300 to the oedometer ring 200. The cutting tool 300 may further include cutting teeth, sharp ends, or other cutting structures on the ring body 320 for improving the efficiency when trimming the soil sample.

The testing device 10 of the present disclosure adopts the modular concept, various kinds of sensing modules can be mounted to the testing cell 20 for characterizing the soil properties of the soil sample. Advantageously, the plurality of needle probes 400 is detachably mountable to the plurality of channels 221 from outside the oedometer ring 200, for performing soil properties measurements. The plurality of needle probes 400 is configured to simultaneously measure the pore water pressures at the selected angles of the oedometer ring 200 for avoiding adverse effects due to time-lag when compared to sequential measurements of the pore water pressures. This allows the measured pore water pressures to be augmented to obtain a more-reliable measurement of pore water pressure of the soil sample. The plurality of needle probes 400 is configured to house a plurality of pore water pressure-measuring sensors 440 used for performing simultaneous measurement of the pore water pressures. An individual needle probe 400 is accessible to the soil sample through a respective hole 220, which has a diameter greater than the diameter of the tube 410 of the individual needle probe 400 by at least 1 mm for avoiding clogging of soil particles. The respective hole 220 has a length at least 0.5 mm longer than the length of the tube 410 for allowing filtering materials to be placed in the respective hole 220. Therefore, this configuration allows the individual needle probe 400 to measure a corresponding pore water pressure present at the respective hole 220, which can further be used to determine $c_v$.

Figure 6:
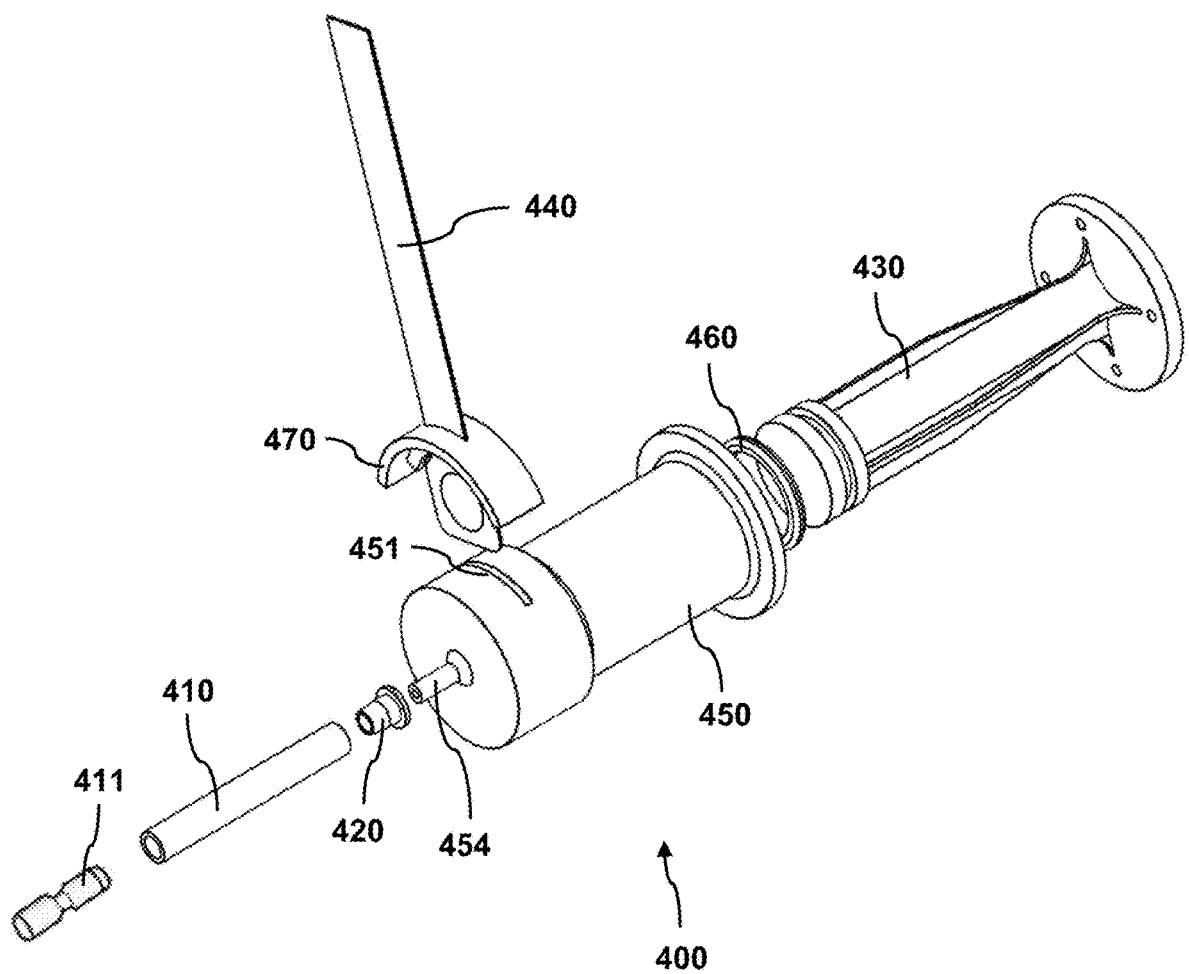
FIG. 6 depicts a perspective view of the needle probe in accordance with certain embodiments of the present disclosure.

FIG. 6 depicts a perspective view of an individual needle probe 400 in accordance with certain embodiments of the present disclosure. The needle probe 400 comprises a barrel 450, a plunger 430, and a sensor holder 440. The barrel is in a cylindrical shape for filling with de-aired water. The tube 410 is coupled to the barrel 450 for receiving the de-aired water such that the de-aired water is accessible to the soil sample. A valve 411 may be coupled to the tube 410 for controlling the flow of de-aired water. The needle probes 400 produce a pore water pressure measuring system of low volumetric compliance. The needle probe 400 can also mimic the structure of a syringe, which takes advantage of such design for effective removal of air bubbles.

Figure 7:
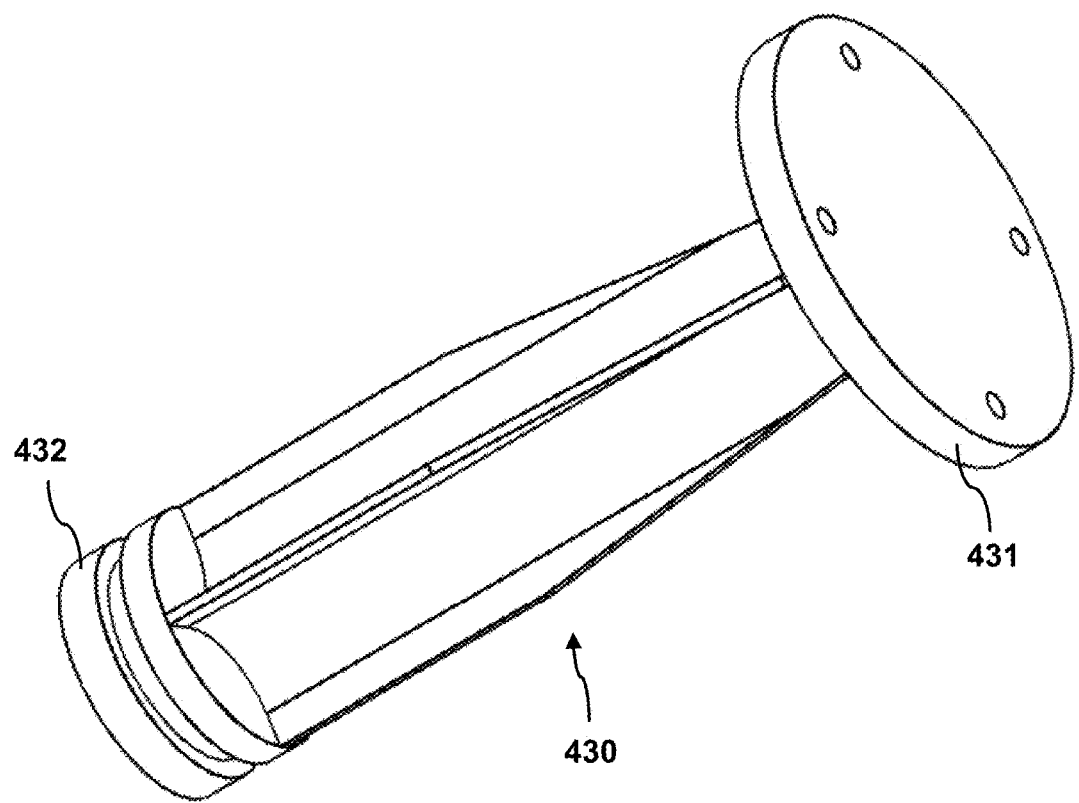
FIG. 7 depicts a perspective view of the plunger of the needle probe of FIG. 6.

The plunger 430 is illustrated in FIG. 7, which is coupled to the barrel 450 by placing a piston end 432 of the plunger 430 into the barrel 450 for pushing the de-aired water forward to fill up the individual needle probe 400. Therefore, the air bubbles from the individual needle probe 400 is removed, and the de-aired water is caused to be pressurized from the pore water. The other end of the plunger 430 is a handle end 431.

Figure 8:
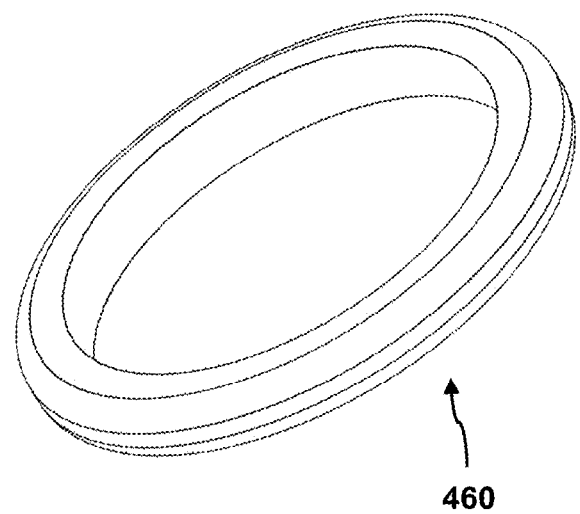
FIG. 8 depicts a perspective view of the O-ring of the needle probe of FIG. 6.

A stiff O-ring 460, as depicted in FIG. 8, is positioned at the piston end 432 of the plunger 430 and used as a plunger stopper for sealing the barrel 450 of the individual needle probe 400. The stiff O-ring 460 can prevent the de-aired water from flowing out or air from flowing into the individual needle probe 400.

Figure 9:
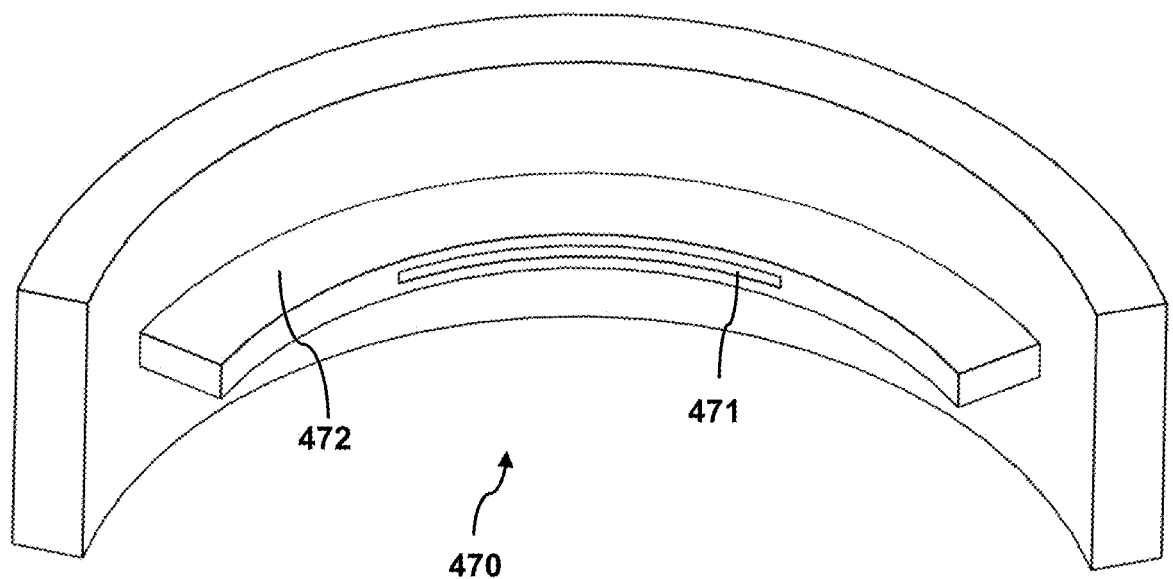
FIG. 9 depicts a perspective view of the sensor holder housed in the needle probe of FIG. 6.
Figure 10:
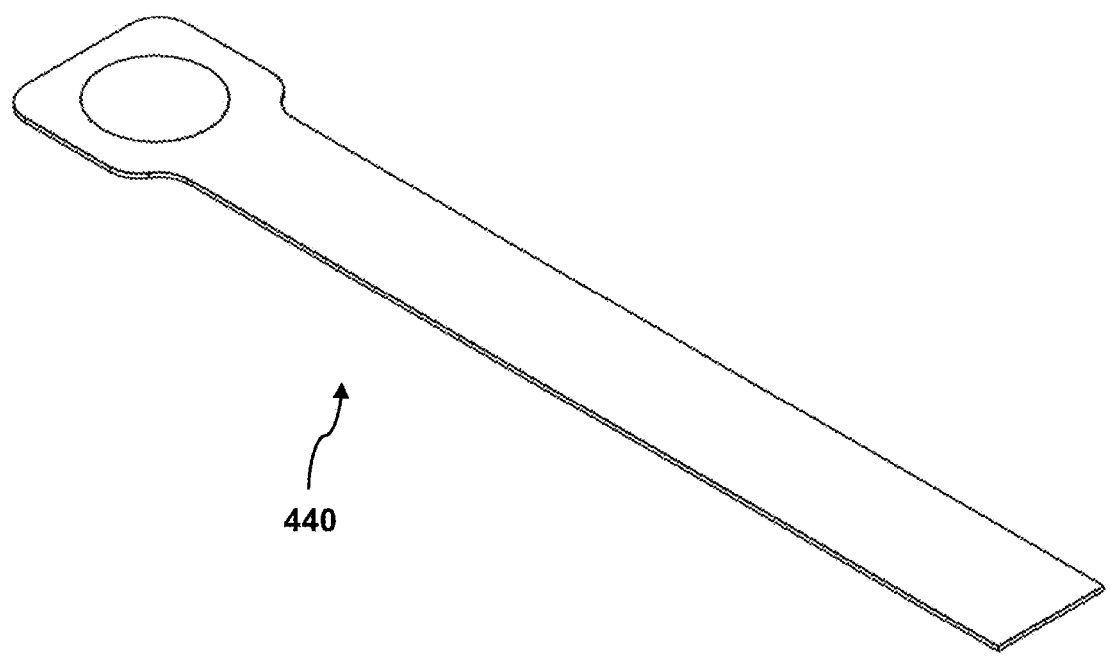
FIG. 10 depicts a perspective view of the pore water pressure-measuring sensor of the needle probe of FIG. 6.

The sensor holder 470 is shown in FIG. 9, which is configured to receive a respective pore water pressure-measuring sensor 440 of FIG. 10. The sensor holder 470 can properly position the respective pore water pressure-measuring sensor 440 into the barrel 450, allowing the respective pore water pressure-measuring sensor 440 to measure the corresponding pore water pressure. In certain embodiments, the sensor holder 470 is a curved member that can be connected to the barrel 450 for securing the respective pore water pressure-measuring sensor 440 in position. The sensor holder 470 has a curved protrusion 472 that can be inserted into the opening 451 of the barrel 450, with a narrow gap 471 thereon that can allow the respective pore water pressure-measuring sensor 440 to pass through. The narrow gap 471 may have a height of 0.5 mm and a width of 13 mm. Preferably, epoxy is used to seal the narrow gap 471 after installing the pore water pressure-measuring sensor 440 for preventing leakage. In certain embodiments, the sensor holder 470 is formed as an integral part of the barrel 450. In certain embodiments, the pore water pressure-measuring sensors 440 and the lateral pressure-measuring sensors 600 may be of the same type or of different types. Preferably, similar to the lateral pressure-measuring sensor 600, the pore water pressure-measuring sensor 440 is a piezoresistive force sensor or a piezoelectric force sensor. Preferably, the pore water pressure-measuring sensor 440 is also coated with three or four polyurethane coatings and a super hydrophobic coating for waterproofing the pore water pressure-measuring sensor 440. Similar calibration is also needed before installation.

In certain embodiments, the pore water pressure-measuring sensor 440 is a Flexiforce® sensor used to gauge Δu measurement. The use of this sensor can avoid deformation problem in the diaphragm of other conventional pressure transducers.

Figure 11:
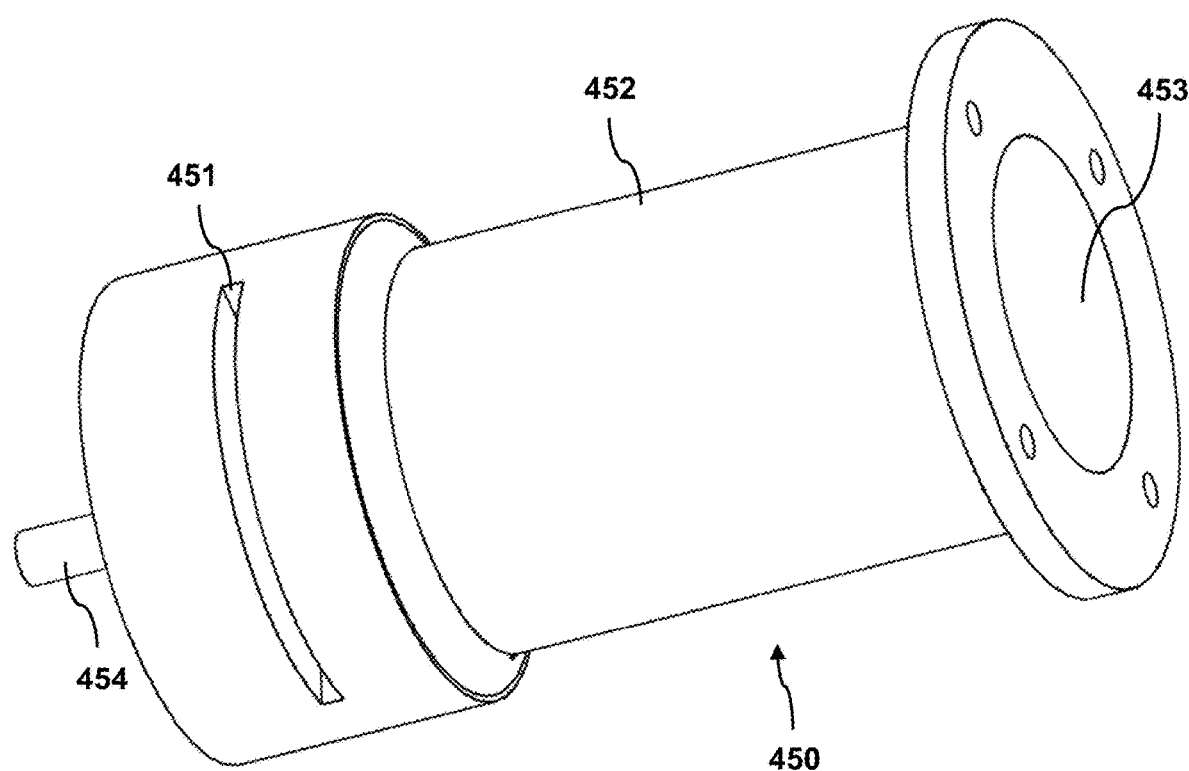
FIG. 11 depicts a perspective view of the barrel of the needle probe of FIG. 6.
Figure 12:
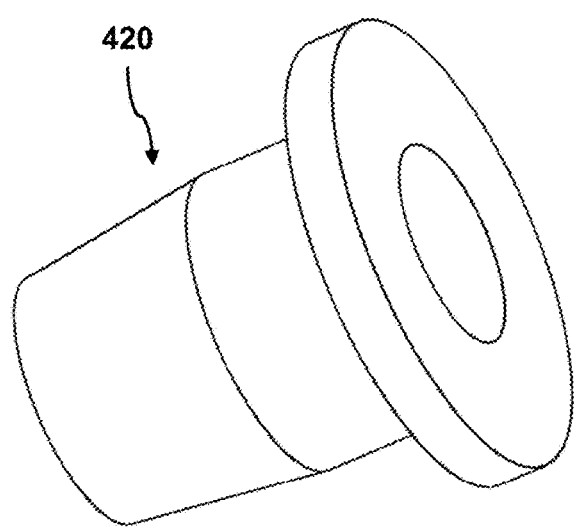
FIG. 12 depicts a perspective view of the tube adapter of the needle probe of FIG. 6.

The barrel 450, according to certain embodiments, is illustrated in FIG. 11. The barrel 450 has a cylindrical tube 452 for filling with de-aired water, an opening 451 for the sensor holder 470 to mount thereon, a tip 454, and a plunger end 453. The wall of the lower part of the cylindrical tube 452 is thicker than the upper part for enhancing the rigidity of the needle probe 400 for installing the sensor holder 470. The plunger 430 is insertable into the barrel 450 from the plunger end 453. The tip 454 is an opposite end to the plunger end 453 longitudinally for discharging the de-aired water to the tube 410. In certain embodiments, the tip 454 and the tube 410 are connected using a tube adapter 420 of FIG. 12.

Figure 13:
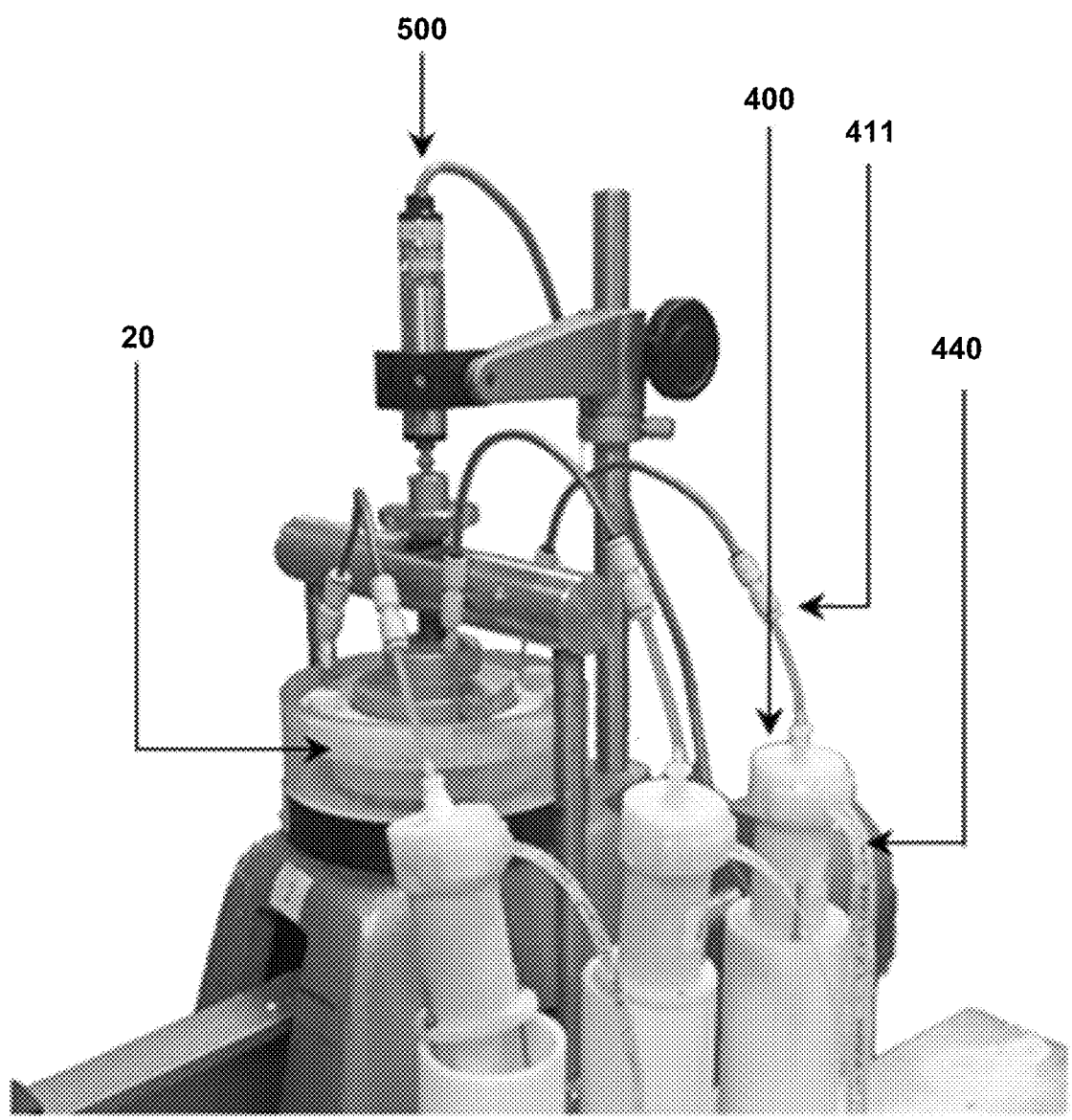
FIG. 13 is a photo of the testing device in accordance with certain embodiments of the present disclosure.

Before the needle probe 400 can be used, the barrel 450 is first saturated with de-aired water, followed by pushing the plunger 430 forward until water comes out from the tube 410 to ensure air bubbles are completely removed from the needle probe 400. The plunger 430 is then firmly fixed in position with stainless-steel bars and clamping nuts to avoid any unnecessary movement (deformation) when the water in the barrel 430 is pressurized during one-dimensional consolidation tests. FIG. 13 shows an experimental setup of soil consolidation in accordance with certain embodiments of the present disclosure. A stress-applying mechanism 500 is provided in the testing device for applying a stress to the soil sample to compress the soil sample. A displacement-measuring sensor is also provided for sensing a displacement made in compressing the soil sample. In certain embodiments, the displacement-measuring sensor is a dial gauge or a linear variable displacement transducer.

The following setup is illustrating one possible implementation of the testing device for performing oedometer tests in accordance with certain embodiment of the present disclosure. The soil sample is first prepared for trimming and fitted into the testing cell 20. Before trimming, filter paper or wire gauze is placed at each of the plurality of holes 220 of the oedometer ring 200 to minimize the possibility of clogging by soil particles. Also, silicone grease may be applied on the inner part of the oedometer ring 200 to reduce the side friction. Afterward, the testing cell 20, with the trimmed soil sample, is installed on a loading frame of the oedometer device. Three 3D-printed needle probes 400 are connected to the three holes 220 of the oedometer ring 200 to measure the excess pore water pressure upon consolidation, and an LVDT is installed to measure the associated vertical displacement of the soil sample. Two lateral pressure-measuring sensors 600 are placed on the inner wall of the oedometer ring 200 to measure the horizontal stress.

This illustrates the multifunctional and modular geotechnical testing device for performing oedometer testing in accordance with the present disclosure. It will be apparent that variants of the above-disclosed and other features and functions, or alternatives thereof, may be combined into many other devices. The present embodiment is, therefore, to be considered in all respects as illustrative and not restrictive. The scope of the disclosure is indicated by the appended claims rather than by the preceding description, and all changes that come within the meaning and range of equivalency of the claims are therefore intended to be embraced therein.

LIST OF REFERENCES

There follows a list of references that are occasionally cited in the specification. Each of the disclosures of these references is incorporated by reference herein in its entirety.

[1] Aldrich, H. P. 1951. Analysis of foundation stresses and settlements at the Hayden Library Harl Preslar Aldrich. Ph.D. dissertation, Massachusett Institute of Technology, Cambridge, Massachusetts, United States.
[2] Al-Zoubi, M. S. 2008. Coefficient of consolidation by the slope method. Geotechnical Testing Journal, 31(6): 1-5.
[3] Al-Zoubi, M. S. 2010. Consolidation analysis using the settlement rate-settlement (SRS) method. Applied Clay Science, 50: 34-40.
[4] Al-Zoubi, M. S. 2014. Consolidation analysis by the modified slope method Geotechnical Testing Journal, 37(3): 540-547.
[5] BS 1377. 1960. British standard methods of test for Soils for civil engineering purpose. Part 6. Consolidation and permeability tests in hydraulic cells and with pore pressure measurement. British Standards Institution, London.
[6] Burland, J. B. and Roscoe, K. H. 1969. Local strains and pore pressures in a normally consolidated clay layer during one-dimensional consolidation. Geotechnique, 19(3): 335-356.
[7] Casagrande, A. and Fadum, R. E. 1940. Notes on soil testing for engineering purposes. Harvard University, Cambridge, USA.
[8] Cour, F. R. 1971. Inflection point method for computing consolidation coefficient. Journal of Soil Mechanics and Foundatitons Div, 97, No. 5, 827-831.
[9] Feng, T.-W. and Lee, Y.-J. 2001. Coefficient of consolidation from the linear segment of the t½ curve. Canadian Geotechnical Journal, 38: 901-909.
[10] Gao, Y., Wang, Y. H. and Chow, J. K. 2017. Application of Film-like sensors for K0 and pore water pressure measurement in clay during 1D consolidation. Geotechnical Testing Journal. doi: 10.1520/GTJ20160008.
[11] Gibson, R. E. 1963. An analysis of system flexibility and its effect on time-lag in pore-water pressure measurements. Géotechnique, 13(1): 1-11.
[12] Helenelund, K. V. 1972. Pore pressures during the consolidation of highly compressible soils. Rakenteiden Mekaniikka, 5(3): 159-174.
[13] Hvorslev, M. J. 1951. Time-lag and soil permeability in ground-water observations. Bulletin No. 36, Waterways Experiment Station, Corps of Engineers, U.S. Army, Vicksburg, Mississippi.
[14] Kutter, B. L., Sathialingam, N. and Hermann, L. R. 1990. Effects of arching on response time of miniature pore pressure transducer in clay. Geotechnical Testing Journal, 13(3), 164-178.
[15] Lovisa, J. and Sivakugan, N. 2013. An in-depth comparison of cv values determined using common curve-fitting techniques. Geotechnical Testing Journal, 36(1): 1-10.
[16] McKinley, J. D. and Sivakumar, V. 2009. Coefficient of consolidation by plotting velocity against displacement. Géotechnique, 59(6): 553-557.
[17] Mesri, G., Feng, T. W. and Shahien, M. 1999. Coefficient of consolidation by inflection point method. Journal of Geotechnical and Geoenvironmental Engineering, 125 (8), 716-718.
[18] Mersi, G., Hayat T. M. 1993. The coefficient of earth pressure at rest. Canadian Geotechnical Journal, 30(4), 647-666.
[19] Mitchell, J. K. and Soga, K. 2005. Fundamentals of soil behavior, John Wiley & Sons, Inc., Hoboken, New Jersey.
[20] Pandian, N. S., Sridharan, A. and Kumar, K. S. 1992. A new method for the determination of coefficient of consolidation. Geotechnical Testing Journal, 15(1): 74-79.
[21] Parkin, A. K. 1978. Coefficient of consolidation by the velocity method. Géotechnique, 28(4): 472-474.
[22] Perloff, W. H., Nair, K. and Smith, J. G. 1965. Effect of measuring system on pore water pressures in the consolidation test. In Proceedings of the 6th International Conferences on Soil Mechanics and Foundation Engineering, Montreal, pp. 338-341.
[23] Robinson, R. G. 1997. Consolidation analysis by an inflection point method. Géotechnique, 47(1), 199-200.
[24] Robinson, R. G. and Allam, M. M. 1996. Determination of coefficient of consolidation from early stage of Log t plot. Geotechnical Testing Journal, 19(3): 316-320.
[25] Robinson, R. G. 1999. Consolidation analysis with pore water pressure measurements. Géotechnique, 49(1): 127-132.
[26] Robinson, R. and Soundara, B. 2008. Coefficient of consolidation from mid-plane pore pressure measurements. International Journal of Geotechnical Engineering, 2(4): 419-425.
[27] Rowe, P. W. and Barden, L. 1966. A new consolidation cell. Géotechnique, 16(2): 162-170.
[28] Sebai, S. and Belkacemi, S. 2016. Consolidation coefficient by combined probabilistic and least residuals methods. Geotechnical Testing Journal, 39(5), 891-897.
[29] Shogaki, T. and Nochikawa, Y. 2004. Triaxial strength properties of natural deposits at K0 consolidation state using a precision triaxial apparatus with small size specimens. Soils Foundations, 44(2), 41-52.
[30] Sivaram, B. and Swamee, P. K. 1977. A computational method for consolidation-coefficient. Soils and Foundations, 17(2): 48-52.

[31] Sridharan, A. and Prakash, K. 1993. δ-t/δ method for the determination of coefficient of consolidation. Geotechnical Testing Journal, 16(1), 131-134.

[32] Sridharan, A. and Prakash, K. 1998. Determination of coefficient of consolidation: a user friendly approach. Ground Engineering, 31(2): 30-32.

[33] Sridharan, A., Murthy, N. S. and Prakash, K. 1987. Rectangular hyperbola method of consolidation analysis. Géotechnique, 37(3): 355-368.

[34] Taylor, D. W. 1948. Fundamentals of soil mechanics, John Wiley & Sons, Inc., New York.

[35] Teerachaikulpanich, N., Okumara, S., Matsunaga, K. and Ohta, H. 2007. Estimation of coefficient of earth pressure at rest using modified oedometer test. Soils Foundation, 47(2), 349-360.

[36] Terzaghi, K. 1943. Theoretical soil mechanics, John Wiley & Sons, Inc., New York.

[37] Tewatia, S. K. 1998. Evaluation of true cv and instantaneous cv, and isolation of secondary consolidation. Geotechnical Testing Journal, 21(2): 102-108.

[38] Tsuchida, T. and Kikuchi, Y. 1991. K0 consolidation of undisturbed clays by means of triaxial cell. Soils Foundation, 31(3), 127-137.

[39] Vinod, J. S. and Sridharan, A. 2015. Laboratory determination of coefficient of consolidation from pore water pressure measurement. Géotechnique Letters, 5: 294-298.

[40] Watabe, Y., Tanaka, M., Tanaka, H. and Tsuchida, T. 2003. K0-consolidation in a triaxial cell and evaluation of in situ K0 for marine clays with various characteristics. Soils Foundation, 43(1), 1-20.

[41] Whitman, R. V., Richardson, A. M. and Healy, K. A. 1961. Time-lags in pore pressure measurements. In Proceedings of the 5th International Conference on Soil Mechanics and Foundation Engineering, Paris, pp. 407-411.

[42] Zeng, X. and Grolewski, B. 2005. Measurement of Gmax and estimation of K0 of saturated clay using bender elements in an oedometer. Geotechnical Testing Journal, 28(3), 264-274.

What is claimed is:

1. A multifunctional and modular geotechnical testing device for testing a soil sample, the testing device comprising:
   a testing cell comprising an oedometer ring for accommodating the soil sample, the oedometer ring including a plurality of holes located on and angularly distributed over an internal lateral surface of the oedometer ring, the plurality of holes forming a plurality of channels to access the soil sample from outside the oedometer ring for measuring pore water pressures at plural selected angles of the oedometer ring; and
   a plurality of needle probes detachably mountable to the plurality of channels from outside the oedometer ring, the plurality of needle probes being configured to simultaneously measure the pore water pressures at the selected angles of the oedometer ring for avoiding adverse effects due to time-lag when compared to sequential measurements of the pore water pressures, wherein the plurality of needle probes is configured to house a plurality of pore water pressure-measuring sensors used for performing simultaneous measurement of the pore water pressures at each hole of the plurality of holes, wherein each needle probe of the plurality of needle probes is configured to house a corresponding pore water pressure-measuring sensor of the plurality of pore water pressure-measuring sensors.

2. The testing device of claim 1 further comprising a plurality of lateral pressure-measuring sensors removably attachable to an inner peripheral side of the testing cell, the plurality of lateral pressure-measuring sensors being arranged to be located at plural selected locations of the inner peripheral side of the testing cell for measuring lateral pressures of the soil sample at the selected locations when the plurality of lateral pressure-measuring sensors is immersed in the soil sample.

3. The testing device of claim 2, wherein:
   each individual lateral pressure-measuring sensor is a piezoresistive force sensor or a piezoelectric force sensor.

4. The testing device of claim 2, wherein:
   each individual lateral pressure-measuring sensor is coated with three or four polyurethane coatings and a super hydrophobic coating for waterproofing the individual lateral pressure-measuring sensor.

5. The testing device of claim 1, wherein each individual needle probe is accessible to the soil sample through a respective hole for measuring a corresponding pore water pressure present at the respective hole, each individual needle probe comprising:
   a barrel for filling with de-aired water;
   a tube insertable into the respective hole, the tube being coupled to the barrel for receiving the de-aired water such that the de-aired water is accessible to the soil sample;
   a plunger coupled to the barrel for pushing the de-aired water forward to fill up the individual needle probe so as to remove air bubbles from the individual needle probe, causing the de-aired water to be pressurized from the pore water; and
   a sensor holder configured to receive a respective pore water pressure-measuring sensor and position the respective pore water pressure-measuring sensor into the barrel, allowing the respective pore water pressure-measuring sensor to measure the corresponding pore water pressure.

6. The testing device of claim 5 further comprising:
   the plurality of pore water pressure-measuring sensors for measuring the pore water pressures at the selected angles of the oedometer ring.

7. The testing device of claim 6, wherein:
   the respective pore water pressure-measuring sensor is a piezoresistive force sensor or a piezoelectric force sensor.

8. The testing device of claim 6, wherein:
   the respective pore water pressure-measuring sensor is coated with three or four polyurethane coatings and a super hydrophobic coating for waterproofing the respective pore water pressure-measuring sensor.

9. The testing device of claim 5, wherein the plurality of pore water pressure-measuring sensors and the plurality of lateral pressure-measuring sensors use pressure-measuring sensors of a same type.

10. The testing device of claim 5, wherein the individual needle probe further comprises:
    a stiff O-ring positioned at an end of the plunger and used as a plunger stopper for sealing the individual needle probe, thereby preventing the de-aired water from flowing out or air from flowing into the individual needle probe.

11. The testing device of claim 5, wherein:
    the respective hole has a diameter greater than a diameter of the tube of the individual needle probe by at least 1 mm for avoiding clogging of soil particles; and the respective hole has a length at least 0.5 mm longer than a length of the tube for allowing filtering materials to be placed in the respective hole.

12. The testing device of claim 1, wherein the plurality of holes is substantially-evenly distributed angularly over the internal lateral surface of the oedometer ring.

13. The testing device of claim 12, wherein the plurality of holes consists of three holes.

14. The testing device of claim 1, wherein each individual hole comprises a channel and a large-diameter end for placing of filter materials to avoid clogging.

15. The testing device of claim 1, wherein the testing cell further comprises:
a top flange for holding the oedometer ring in position and preventing any external interference that potentially changes boundaries and loading conditions of the soil sample.

16. The testing device of claim 1, wherein the testing cell further comprises a cutting tool mountable on the oedometer ring for trimming the soil sample to be used in testing.

17. The testing device of claim 16, wherein the cutting tool is made of stainless steel.

18. The testing device of claim 16, wherein the oedometer ring further includes a plurality of grooves configured to receive the cutting tool for securing the cutting tool to the oedometer ring.

19. The testing device of claim 1, wherein the oedometer ring is cylindrical in shape such that the soil sample is in a form of disc.

20. The testing device of claim 1 further comprising:
a stress-applying mechanism for applying a stress to the soil sample to compress the soil sample; and
a displacement-measuring sensor for sensing a displacement made in compressing the soil sample.

21. The testing device of claim 20, wherein the displacement-measuring sensor is a dial gauge or a linear variable displacement transducer.

* * * * *